(12) United States Patent
Crooks et al.

(10) Patent No.: US 11,903,431 B2
(45) Date of Patent: Feb. 20, 2024

(54) LOUPE-FACE SHIELD PROTECTOR

(71) Applicant: Monica Crooks, Granite Bay, CA (US)

(72) Inventors: Monica Crooks, Granite Bay, CA (US); Paul J. Soo, Elk Grove, CA (US); Stephen Montero, Richardson, TX (US)

(*) Notice: Subject to any disclaimer, the term of this patent is extended or adjusted under 35 U.S.C. 154(b) by 340 days.

(21) Appl. No.: 17/232,032

(22) Filed: Apr. 15, 2021

(65) Prior Publication Data
US 2021/0329998 A1  Oct. 28, 2021

Related U.S. Application Data

(60) Provisional application No. 63/028,790, filed on May 22, 2020, provisional application No. 63/101,268, filed on Apr. 22, 2020.

(51) Int. Cl.
*A41D 13/11* (2006.01)
*A41D 31/32* (2019.01)
(Continued)

(52) U.S. Cl.
CPC ...... *A41D 13/1184* (2013.01); *A41D 13/1161* (2013.01); *A41D 31/32* (2019.02);
(Continued)

(58) Field of Classification Search
CPC ............ A41D 13/1161; A41D 13/1138; A41D 2400/44; A41D 13/1184; A41D 13/1107; A41D 13/11–1192; A62B 18/084; A62B 23/025; A62B 17/04; A62B 18/00; A62B 18/02; A62B 18/025; A62B 18/08; A62B 18/082; A61F 9/045; A61F 9/04–08; A61B 90/05; A61B 2090/3616; A61B 2090/502; A61B 90/30; G02C 7/086; G02C 9/04; G02C 7/088; A42B 3/225
See application file for complete search history.

(56) References Cited

U.S. PATENT DOCUMENTS 5,341,513 A * 8/1994 Klein ................. A61F 9/02
                                                    128/857
5,709,459 A * 1/1998 Gourgouliatos ..... G02B 27/281
                                                    362/277
(Continued)

*Primary Examiner* — Alireza Nia
*Assistant Examiner* — Eric Richard McQuiggan
(74) *Attorney, Agent, or Firm* — Temmerman Law; Mathew J. Temmerman

(57) ABSTRACT

A face protecting apparatus for protecting a user from droplets and solids containing bacteria, viruses, and other hazardous materials. The apparatus includes a face shield and a frame member. The face shield includes an elongated planar surface, a plurality of bilateral angled creases and a plurality of openings. The elongated planar surface creates a seal at the user's chest when the user bends forward thereby providing a protective barrier to ejected debris. The bilateral angled creases provide a concave configuration to the face shield that brings the face shield into close proximity to the face of the user. The openings enable a fiber optic LED light and a plurality of loupe magnifiers of a loupe device worn by the user to protrude therethrough thus enabling the user to wear the face protecting apparatus in combination with the loupe device and the fiber optic LED light without any obstruction.

16 Claims, 15 Drawing Sheets

(51) Int. Cl.
*G02C 7/08* (2006.01)
*A61B 90/00* (2016.01)
*A61B 90/50* (2016.01)

(52) U.S. Cl.
CPC .............. *A61B 90/05* (2016.02); *G02C 7/086* (2013.01); *A61B 2090/502* (2016.02)

(56) References Cited

U.S. PATENT DOCUMENTS

| | | | | |
|---|---|---|---|---|
| 6,764,194 B1* | 7/2004 | Cooper | ................. | F21V 21/084 |
| | | | | 362/426 |
| 9,470,908 B1* | 10/2016 | Frankel | .................. | G02C 5/124 |
| 2008/0252893 A1* | 10/2008 | Zuluaga | ................. | A61B 90/36 |
| | | | | 356/445 |

* cited by examiner

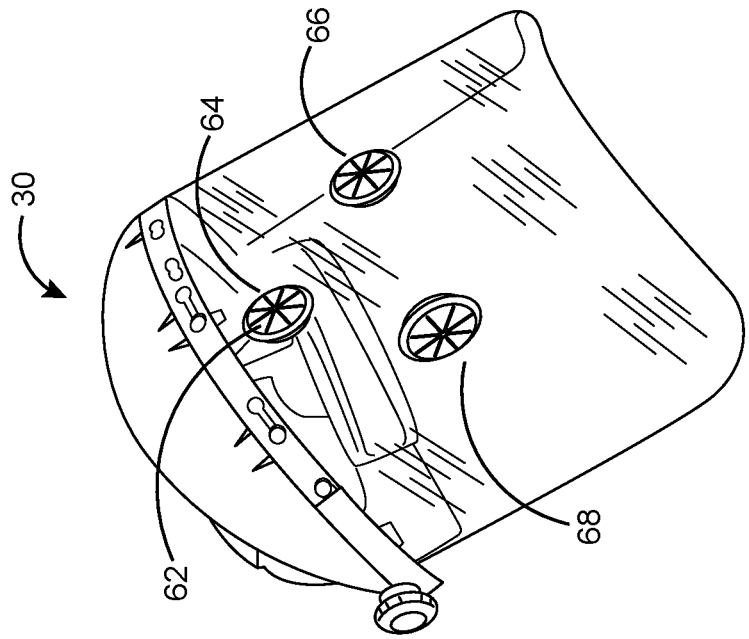
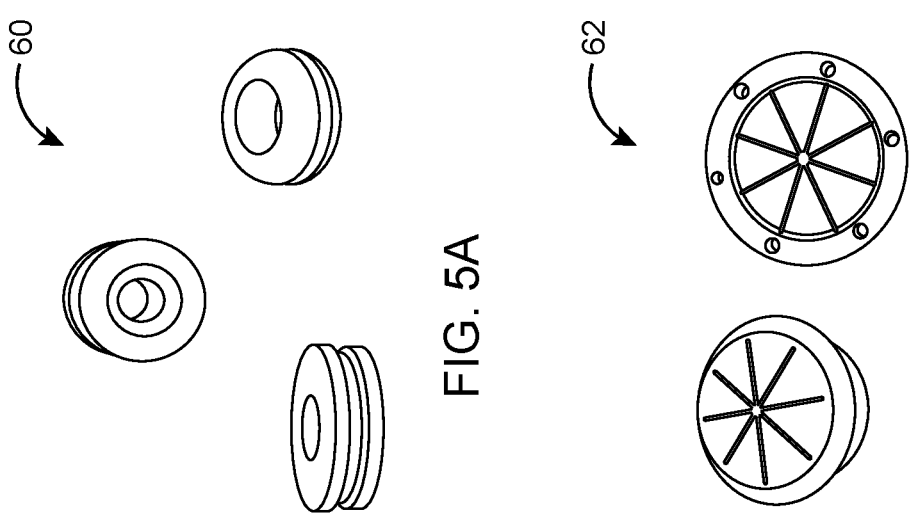
FIG. 5C
FIG. 5A
FIG. 5B

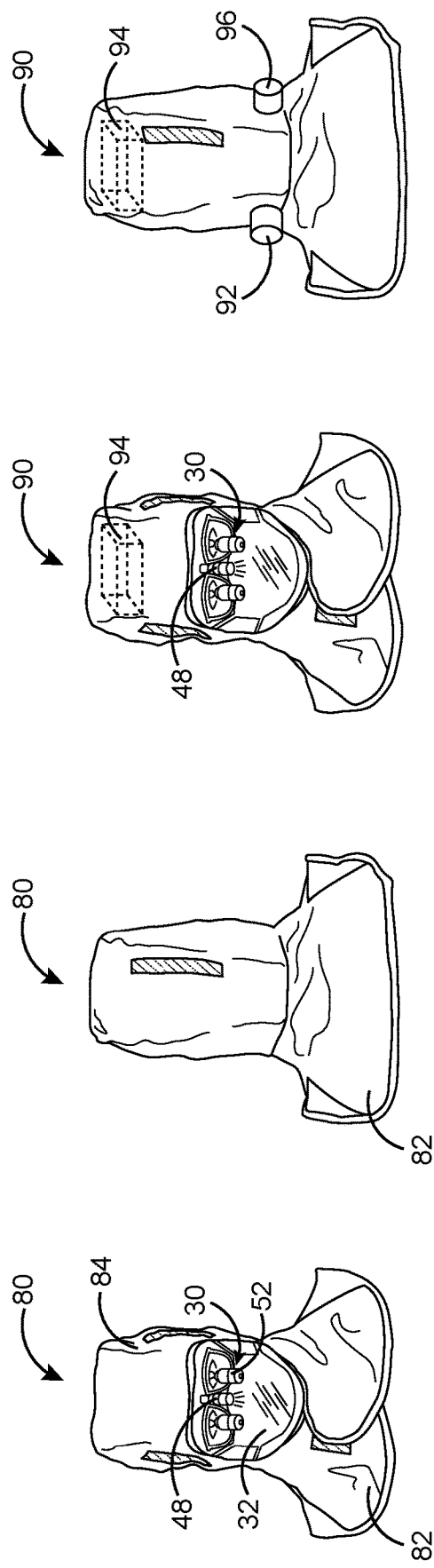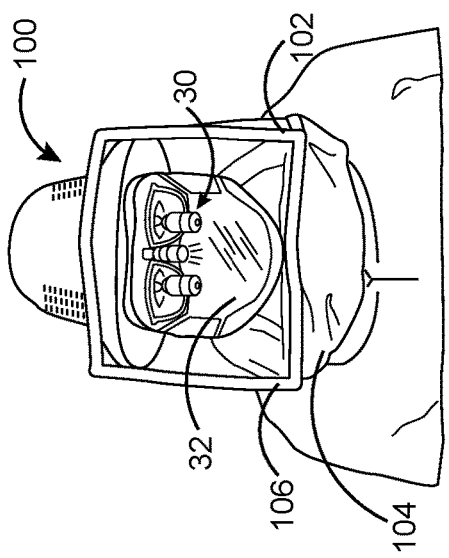
FIG. 7D
FIG. 7C
FIG. 7B
FIG. 7A
FIG. 7E

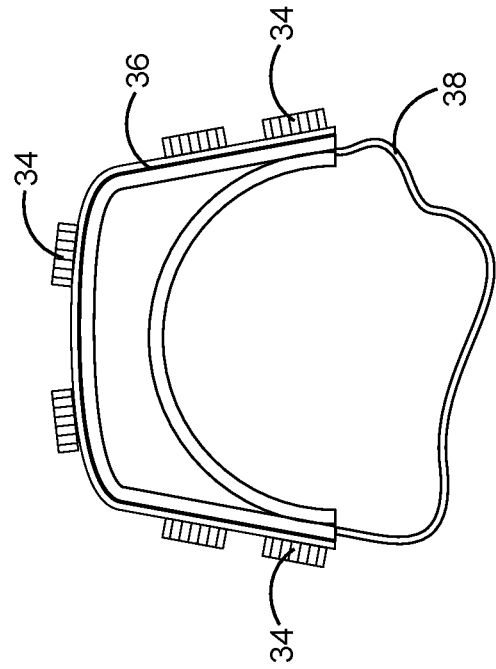
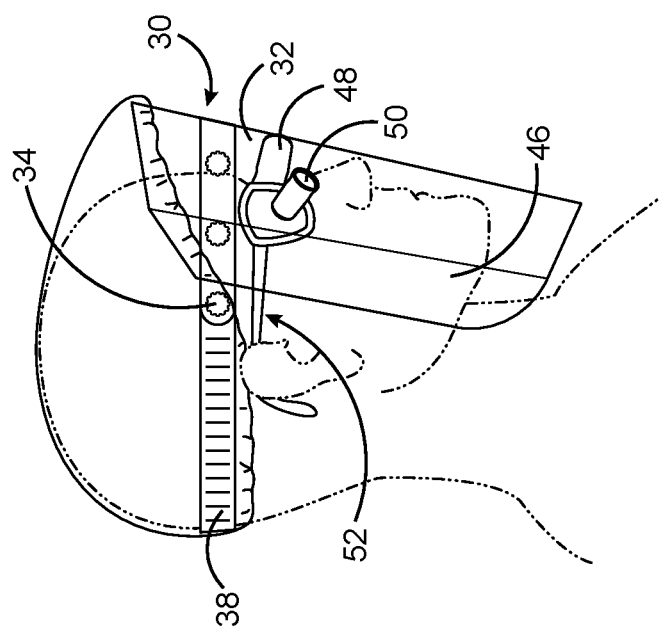
FIG. 10B
FIG. 10A

LOUPE-FACE SHIELD PROTECTOR

RELATED APPLICATIONS

This application claims priority from the United States provisional application with Ser. No. 63/101,268, which was filed on Apr. 22, 2020, and further claims priority from the United States provisional application with Ser. No. 63/028,790 filed May 22, 2020. The disclosures of these provisional applications are incorporated herein as if set out in full.

BACKGROUND OF THE DISCLOSURE

Technical Field of the Disclosure

The present invention relates generally to protective face shields, and more particularly, to a face protecting apparatus shaped to accommodate a loupe device and a fiber optic LED light worn by a user in an unobstructed manner and designed to protect the user from droplets and solids containing bacteria, viruses, and other hazardous materials.

Description of the Related Art

A wide variety of face shields have been developed to protect a user's eyes, nose, lungs and face from various occupational hazards. The face shields are typically utilized as protective equipment in professions such as chemical, medical, construction, and manufacturing. Since such face shields are utilized in different industries, the requirements for protection vary from industry to industry. While one industry may require protection against hazardous chemicals, another may require protection against flying debris, still another may requires protection against extreme temperatures or light, or gasses while others require protection against undesirable physical contact with body fluids and aerosols. Thus, developing a maneuverable face shield that can be utilized for a variety of applications is a challenging task. In addition, some industries require the use of supplemental protection equipment, such as goggles, respirators and hoods with face shields. In these industries, the face shield must be able to accommodate such accessories, in addition to eyewear including magnifiers and lights. In the instance of viral outbreaks and the like, face shields and assemblies must be able to achieve air-tight fits with stringent filtering requirements (~0.3 microns often for aerosolized biological materials) without losing maneuverability. Finally, as people's faces vary widely in size and shape, face shields should be capable of providing protection for different variety of users.

Face shields are typically supported on or about a user's head by a headband, visor, helmet, or neck support with the face shield attached such that it is positioned in front of the user's face during operation. Many face shields can pivot from a lowered position (during use) to an upward position (when not in use), or from an upper position during use, to a lower position when not in use depending upon the positioning of the support frame. Usually, the face shields are worn for an extended period of time. As such, it is important that the face shield be relatively light-weight and comfortable to wear. In addition, as described above, the face shield should provide adequate protection while not limiting visibility. Thus, proper fit is important because it aids in both comfort and protection. The lens of most face shields come into contact with various types of debris, all of which can damage the lens, especially over time. Thus, it is also advantageous if the lens can be replaced, as needed, during use.

The historic outbreak of infectious diseases, in particular those occurring on a global level such as the recent outbreak of the Sars-CoV-2 virus will continue to prompt healthcare providers and officials to look for more aggressive methods to protect both patients and healthcare providers from either catching or further spreading these deadly diseases.

Physicians, dentists and other healthcare workers occasionally must wear fiber optic LED apparatuses and loupe optical magnifiers while examining and treating patients. It would be beneficial for the medical or dental health care individuals if they could wear the fiber optic LED apparatus and the loupe optical magnifiers in conjunction with a full-face protection shield in an unobstructed manner. FIGS. 1A-1C show a few examples of a loupe device 10. FIGS. 2A and 2B show a few examples of a fiber optic LED light 14 including a headgear 16 and a barrel 18 (FIG. 2C) for holding the LED light. With regard to the fiber optic LED light 14 and based on current market technology, the majority require that the LED barrels 18 must be physically positioned closely to the forehead. This is problematic with current market face shield designs as the length of the barrel 18 on most fiber optic LEDs 14 and/or the magnifying loupes 10 is relatively long and impedes proper fitting with the face shields available in the market if the loupe devices 10 are placed underneath the face shield. FIGS. 1A and 1B show examples of the loupe device 10 with embedded optic magnifiers 12. FIG. 1C shows the loupe device 10 with the fiber optic LED light 14 attached to an eye frame 20. Placing the entire LED barrel 18 external to the face shield in any manner is also very problematic since the additional projected distance outward disturbs the intended focal point of the light beam. Also, the inter-pupillary distance for proper focus is specific to the individual, and every individual is different. It is impractical and unnecessary to make face shields that are user specific. Furthermore, wearing the fiber optic LED light 14 from behind the shield is problematic due to refraction and other optic anomalies due to interfering properties of the plastic material of the face shield.

Therefore, there is a need for a lightweight and comfortable face protecting apparatus for protecting a user from droplets and solids containing bacteria, viruses, and other hazardous materials. Such an apparatus would be shaped to accommodate a loupe device and a fiber optic LED light worn by the user in an unobstructed manner while treating a patient. Furthermore, such an apparatus would provide a full face shield protection to the user while using the loupe device with longer barrels without impeding the normal fitting of the face shield apparatus over the face. Moreover, such an apparatus would accommodate a ventilation system to protect the user from hazardous materials in close proximity to the breathing space of the user. Further, such an apparatus would be adaptable to integrate with an anti-glare element to alleviate eye strain caused by the reflected light from the fiber optic LED light against the face protecting apparatus. Such an apparatus would include a supporting means for accurately positioning the loupe device and the fiber optic LED light on the face shield. Moreover, such a face shield would provide lasting comfort and desired protection in a variety of applications. The present embodiment overcomes shortcomings in the field by accomplishing these critical objectives.

SUMMARY OF THE INVENTION

To minimize the limitations found in the prior art, and to minimize other limitations that will be apparent upon the reading of the specification, the present disclosure provides a face protecting apparatus shaped to accommodate a loupe device and a fiber optic LED light worn by the user. The face protecting apparatus protects a user from droplets and solids containing bacteria, viruses, and other hazardous materials. The face protecting apparatus includes a frame member secured to the head of the user and a removable face shield connected to the frame member.

Various embodiments of the face protecting apparatus are contemplated on two prototype categories: a first prototype and a second prototype. These two overarching prototype categories include many embodiments that are useful to medical personnel by providing protection against aerosols, droplets, bodily fluid splatter, and projectiles expelled by a patient or in the course of treating a patient in addition to physical protection of the head in certain embodiments. The first prototype is brand specific and adapted to the physical dimensions of any given brand of loupes and/or loupe with fiber optic combination. The second prototype represents a universal fit prototype and is adaptable to nearly any brand of the loupe and fiber optic assembly.

In one embodiment, the protective face shield (clear plastic shield) is removably supported by an outer frame secured at a greater distance from the forehead than from the chin thereby accommodating the dimensions of the projected elements of the loupe and fiber optic systems. The face shield includes a plurality of bilateral angled creases which bring the face shield into closer proximity to the wearer's face. In one configuration of the preferred embodiment, the plurality of bilateral angled creases has an inclination of approximately 45 degrees. The face shield optionally has an approximately 3" dart at a centerline of an upper portion of the shield and is overlapped by about 1" forming a marked concavity inside the shield which better conforms to the face. The face shield slides on and off the forehead with or without utilizing a fastening member for securing the frame member to the head in one embodiment of the second prototype or the face shield slides on and off of the neck, or shoulders, or neck and shoulders in another embodiment thereby making it easy to don and doff. In the first prototype, the face shield is directly clipped onto the brand specific loupes at one point on each of the two ear bars, and centrally at the nose bridge of the loupe frame. The magnifying loupes either fit behind the shield or project through the shield through a plurality of star-cut silicone grommets. Likewise, the fiber optic LED light projects through the plastic face shield through the plurality of star-cut silicone grommets. In one embodiment, of the second prototype, the outer frame is molded as a single, unitary member in such a way as to define and dictate the angle needed to hold the plastic shield at least 3" farther away at the forehead and closer (about 1") to the face at the chin. In another embodiment, the face shield is affixed to a flat rigid outer strap, and the declination angle is established by a system of rotation that creates the declined angle when the face protecting apparatus is flipped downward. In both of these cases, the face shield is attached at the forehead with a nearly circumferential headband with or without elastic adaptation at the back to which the outer frame is connected with rotational knobs allowing the face shield secured on its outer frame to be flipped up and out of the way providing easy access for loupe and fiber optic adjustment. In yet another embodiment, the face shield is affixed to a frame that fits around the neck and/or on the shoulders with the angle of declination defined by the molded frame and extending to an upward direction.

In another embodiment, the face shield is adapted to existing surgical fiber optic headgear that is worn like a helmet on the head by virtue of a plurality of bilateral clips with the rotational knobs allowing the face shield to be flipped up when not in use and down when in use.

All embodiments of the first and the second prototypes provide the advantage of "sealing" to the wearer's chest with a slight bend in the wearer's neck during operation by virtue of an adequate length of the face shield below the chin thereby eliminating a gap for entering potential aerosol below the face shield. The embodiment supported by the neck and shoulder forms an absolute seal at a base of the face shield by virtue of the shield being connected to the frame at the neckline.

The face protecting apparatus effectively combines subcomponents of the face shield with the loupe device and the fiber optic LED light in a novel combination conducive to the proper performance of each component for its intended use without onerous reconfiguration. For example, a plurality of openings in the face shield for the plurality of loupe magnifiers provides a solution for longer optical barrels. Conversely, the plurality of openings may be eliminated for the plurality of magnifiers when using shorter optical or magnifying barrels. Notably, the design may also include punches and templates allowing the user to customize these components without compromising the safety of the user.

Further, a plurality of unique bilateral angled creases creates a concave configuration to the plastic shield thereby allowing close adaptation and proximity to the wearer's face thus offering added isolation and protection from splatter and aerosolized debris. The plurality of bilateral angled creases has an inclination of approximately 45 degrees. The length of the shield is sufficient to touch the wearer's chest with only a slight, comfortable bend of the neck, thus offering more of a seal and barrier to ejected debris from a drill or aerosol producing instrument in use.

It is a first objective of the present invention to provide a face protecting apparatus for protecting a user from droplets and solids containing bacteria, viruses, and other hazardous materials.

A second objective of the present invention is to provide a face protecting apparatus shaped to accommodate a loupe device and a fiber optic LED light worn by the user in an unobstructed manner while treating a patient.

A third objective of the present invention is to provide a face protecting apparatus including a face shield featuring a non-glare upper element adaptable to mitigate eye strain caused by reflected light from the fiber optic LED light against the plastic material of the face shield.

A fourth objective of the present invention is to provide a face protecting apparatus having a face shield that flips up for easy access to the fiber optic LED light to adjust position or to tighten securing screws connected to the face shield.

A fifth objective of the present invention is to provide a face protecting apparatus including a face shield designed to incline toward the chin of the user, and embodying bilateral angled creases and having a dart at the top of the face shield for better face contour conformity and closer face proximity.

A sixth objective of the present invention is to provide a face protecting apparatus featuring a face shield having an elongate length sufficient to easily create a seal at the user's chest with a slight forward bending of the neck thereby providing a protective barrier to ejected debris from an aerosol producing instrument in use by the user.

A seventh objective of the present invention is to provide a face protecting apparatus that facilitates simplified disinfection defined by a "peel-away" feature in which several protective layers are preloaded on the frame and an outermost soiled layer is easily removed between patients.

An eighth objective of the present invention is to provide a face protecting apparatus that is shaped to accommodate a wide range of existing brands of the fiber optic LED light, the loupe device and various headgear designs.

Another objective of the present invention is to provide a face protecting apparatus that provides a full face shield protection to the user while using the loupe device with longer barrels without impeding the normal fitting of the face shield apparatus over the face.

Yet another objective of the present invention is to provide a face protecting apparatus that accommodates a ventilation system to protect the user from hazardous materials in close proximity to the breathing space of the user.

These and other advantages and features of the present invention are described with specificity so as to make the present invention understandable to one of ordinary skill in the art.

BRIEF DESCRIPTION OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention. Thus, the drawings are generalized in form in the interest of clarity and conciseness.

FIG. 5A shows perspective views of a plurality of rubber bushing grommets adaptable to use with the face shield apparatus;

FIG. 5B shows perspective views of examples of a plurality of star-cut flex rubber grommets adaptable to use with the face shield apparatus;

FIG. 5C shows different locations of the plurality of star-cut flex rubber grommets positioned on the face shield in accordance with one embodiment of the present invention;

FIG. 7A shows a front view of a head protector adaptable to use with the face protecting apparatus in accordance with one embodiment of the present invention;

FIG. 7B shows a rear view of the head protector illustrated in FIG. 7A in accordance with one embodiment of the present invention;

FIG. 7C shows a front view of another embodiment of the head protector illustrated in FIG. 7A made of a cleansable material and having a compartment on a top portion thereof in accordance with one embodiment of the present invention;

FIG. 7D shows a rear view of another embodiment of the head protector illustrated in FIG. 7C in accordance with one embodiment of the present invention;

FIG. 7E shows a front view of yet another embodiment of the head protector featuring a ventilated full head protector having an external ventilation system adaptable to use with the face protecting apparatus in accordance with one embodiment of the present invention;

FIG. 10A shows a side view of the face protecting apparatus, illustrating the frame member and the face shield shaped to accommodate the loupe device and the fiber optic LED light worn by the user in accordance with one embodiment of the present invention;

FIG. 10B shows a top view of the face protecting apparatus, illustrating a head band and the plurality of grommets connecting the face shield to a rigid head frame of the head band in accordance with one embodiment of the present invention;

DETAILED DESCRIPTION OF THE DRAWINGS

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized, and changes may be made without departing from the scope of the present invention.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below.

As used herein, the singular forms "a", "an" and "the" include plural referents unless the context clearly dictates otherwise. "And" as used herein is interchangeably used with "or" unless expressly stated otherwise. As used herein, the term 'about" means +/−5% of the recited parameter. All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "wherein", "whereas", "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

Figure 1C:
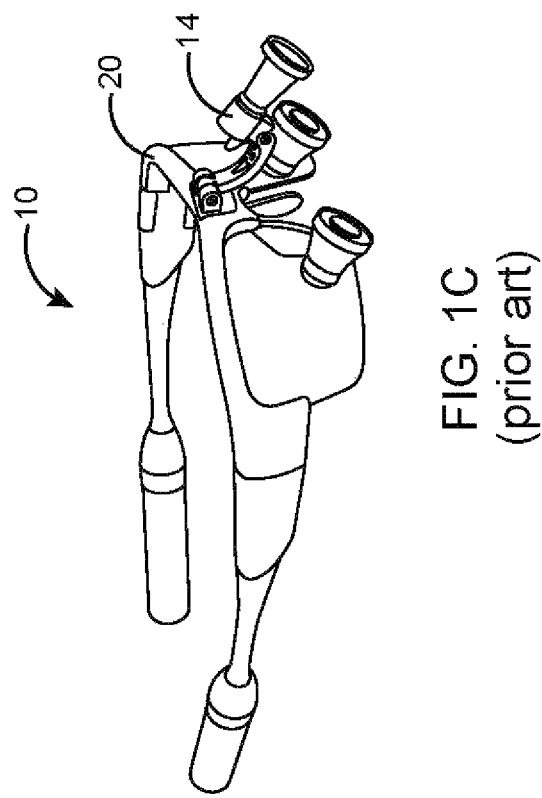
FIG. 1C shows a perspective view of an existing type of a combination of a loupe device and a fiber optic LED light attached to an eye frame.
Figure 1A:
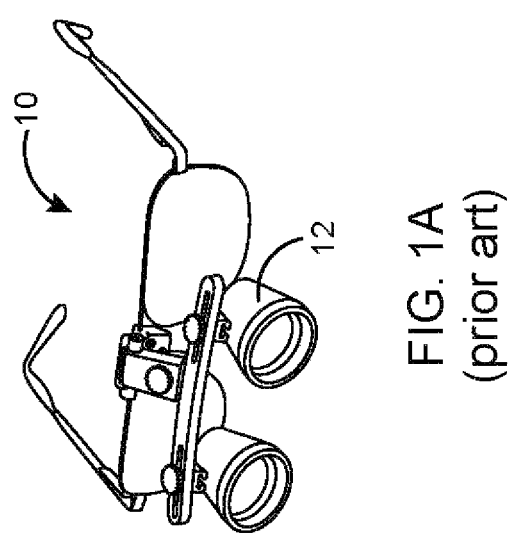
FIGS. 1A and 1B show perspective views of existing type of loupe devices.
Figure 1B:
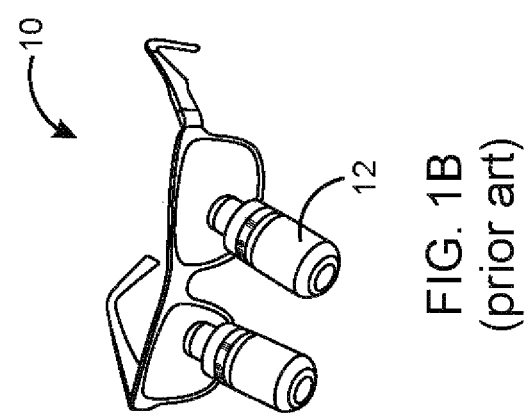
Figure 2B:
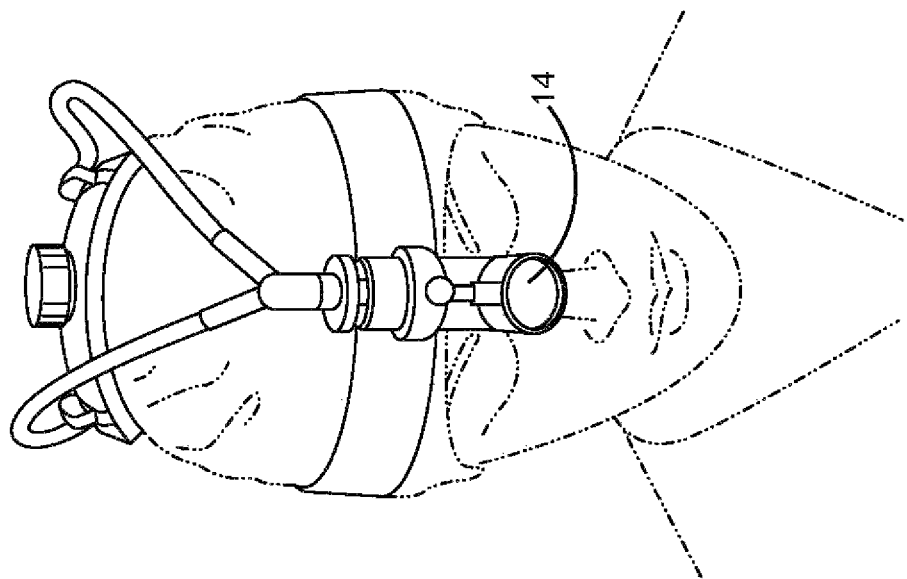
FIG. 2B shows a perspective view of an existing type of a fiber optic LED headgear apparatus in a detached state.
Figure 2A:
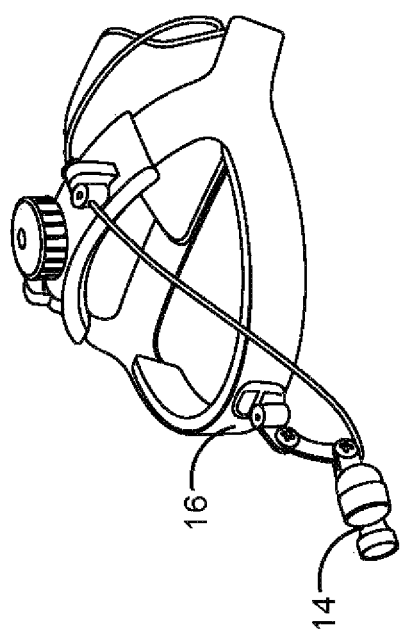
FIG. 2A shows a perspective view of an existing type of a fiber optic LED medical headlight light in an attached state.
Figure 2C:
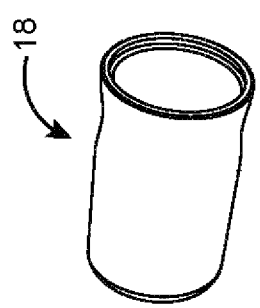
FIG. 2C shows a perspective view of an existing type of a barrel for holding a LED light.
Figure 3B:
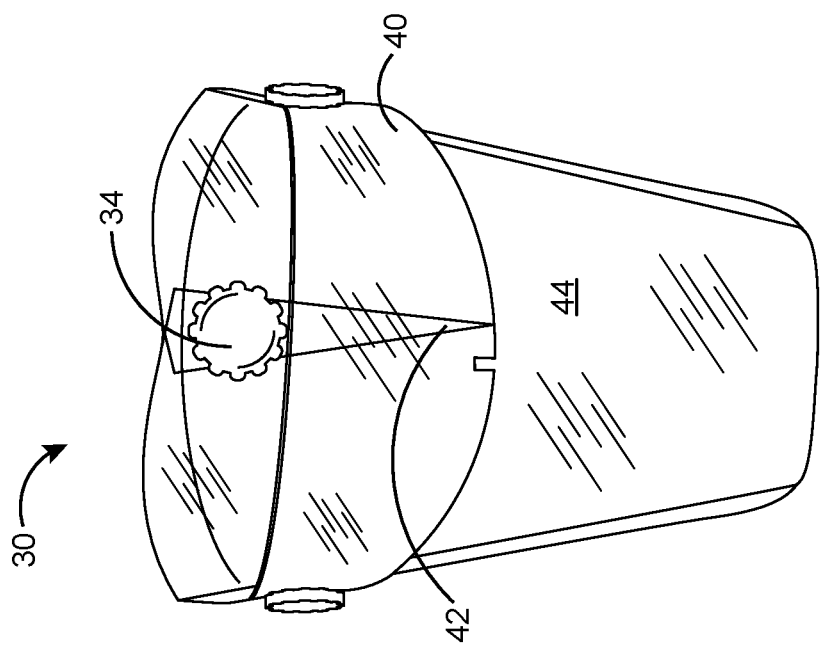
FIG. 3B is a front perspective view of the face protecting apparatus, illustrating a frame member and a face shield of the face protecting apparatus in accordance with one embodiment of the present invention.
Figure 3A:
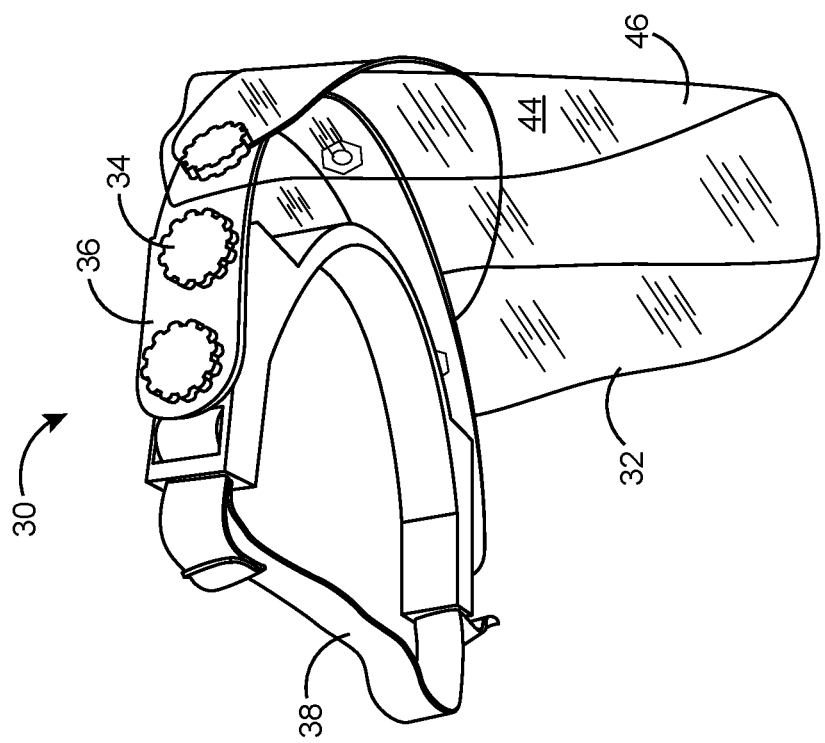
FIG. 3A is a side perspective view of a face protecting apparatus in accordance with one embodiment of the present invention.

Referring to FIGS. 3A and 3B, a face protecting apparatus 30 for protecting a user from droplets and solids containing bacteria, viruses, and other hazardous materials is illustrated. The face protecting apparatus 30 is shaped to accommodate a loupe device 52 and a fiber optic LED light 48 worn by the user. In use, the face shield apparatus 30 provides protection to medical and dental health care providers against aerosols, droplets, bodily fluid splatter and projectiles expelled by a patient or during the course of treating a patient. The face protecting apparatus 30 includes a frame member 36 secured to the head of the user and a removable face shield 32 connected to the frame member 36.

The face shield 32 is connected to the frame member 36 utilizing a plurality of securing members 34 such as a knob. The frame member 36 is secured to the head utilizing at least one adjustable fastening member 38 such as an elastic band as shown in FIG. 3A. The loupe device 52 includes a plurality of loupe magnifiers: a right optic magnifier 50 and a left optic magnifier 51 (see FIG. 11B).

As shown in FIGS. 3A and 3B, the face shield 32 features a plurality of bilateral angled creases 46 adaptable to create a concave configuration to the plastic face shield 32 which allows close adaptation and proximity to the wearer's face thereby providing added isolation and protection from splatter and aerosolized debris. Referring to FIG. 3B, the face protecting apparatus 30 includes a dart member 42 at a centerline of an upper portion of the face shield 32 that forms a concave anatomy inside the face shield 32 that better conforms to the face such that the face shield 32 encapsulates, adheres to and protects the face of the user from hazardous materials.

Figure 11B:
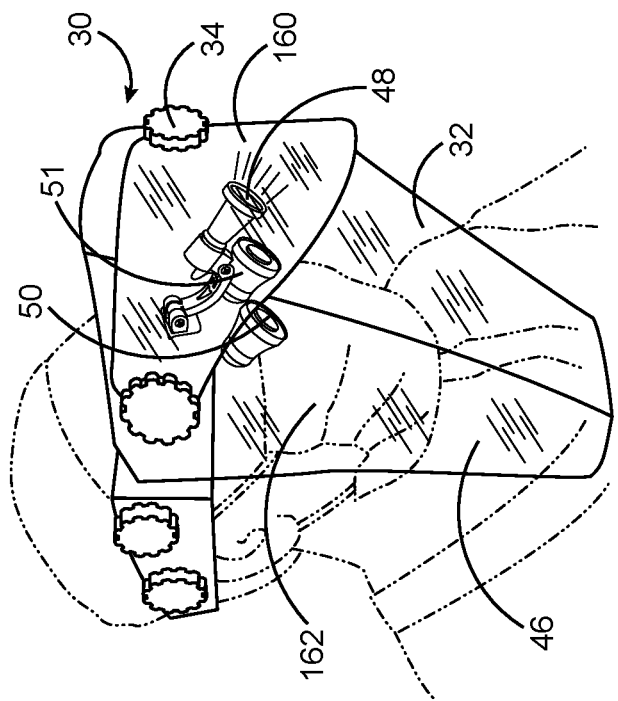
FIG. 11B shows a side perspective view of the face protecting apparatus illustrated in FIG. 11A in accordance with one embodiment of the present invention.
Figure 11A:
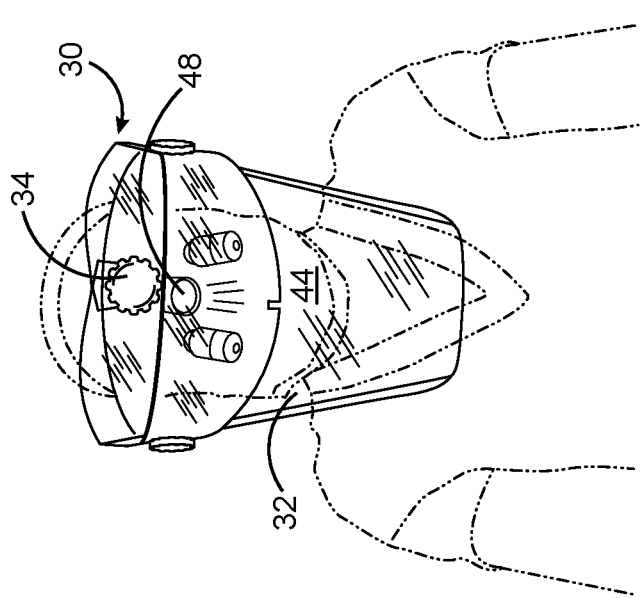
FIG. 11A shows a front perspective view of the face protecting apparatus including the fiber optic LED light in an active state, the loupe device, a plurality of securing members, a surgical mask and a pair of glasses in accordance with one embodiment of the present invention.

The face shield 32 includes an elongated planar surface 44. As shown in FIG. 11A, there exists a gap between the face shield 32 and the user's neck when the head is in an erect position, but this gap disappears when the user bends the neck to treat patients as shown in FIG. 11B. The disappearance of the gap is because of the elongated length of the face shield 32 which is sufficient for the face shield 32 to touch the wearer's chest with only a slight, comfortable bend of the neck thus offering a seal at the user's chest and barrier to ejected debris from a drill or aerosol producing instrument in use by the user. In one aspect of the preferred embodiment, the face shield 32 fits very close to the neck and chest of the user in use such that it minimizes aerosol and particle flow from a given patient to the user during a procedure.

The preferred face protecting apparatus 30 contemplates various configurations with a focus on two prototypes: a first prototype and a second prototype. The first prototype is brand specific and the second prototype is of a universal fitment type. Various embodiments of the present invention are contemplated within each of these two overarching prototype categories. The embodiments categorized under these prototypes are useful to medical personnel by providing protection against highly contagious and infectious diseases expelled by the patient in addition to physical protection of the head. The first prototype represents an embodiment which is operable in conjunction with, for example, the DenMat® brand PeriOptix fiber optic loupes.

The second prototype "Universal fit type" is adaptable to nearly any brand of the loupe device 52 and the fiber optic LED light 48. Importantly, the second prototype eliminates the need for disinfecting the wearer's loupe device 52 and the fiber optic LED light 48, because these elements are all protected behind the face shield 32. In one configuration, the second prototype includes a tinted film 40 as shown in FIGS. 3A and 3B or a non-glaring plastic polarized film or a non-glaring film integrated into an uppermost dimension of the plastic material of the face shield 32 reduces reflected glare from the fiber optic LED light 48 that shines on the plastic material behind the face shield 32.

Figure 4:
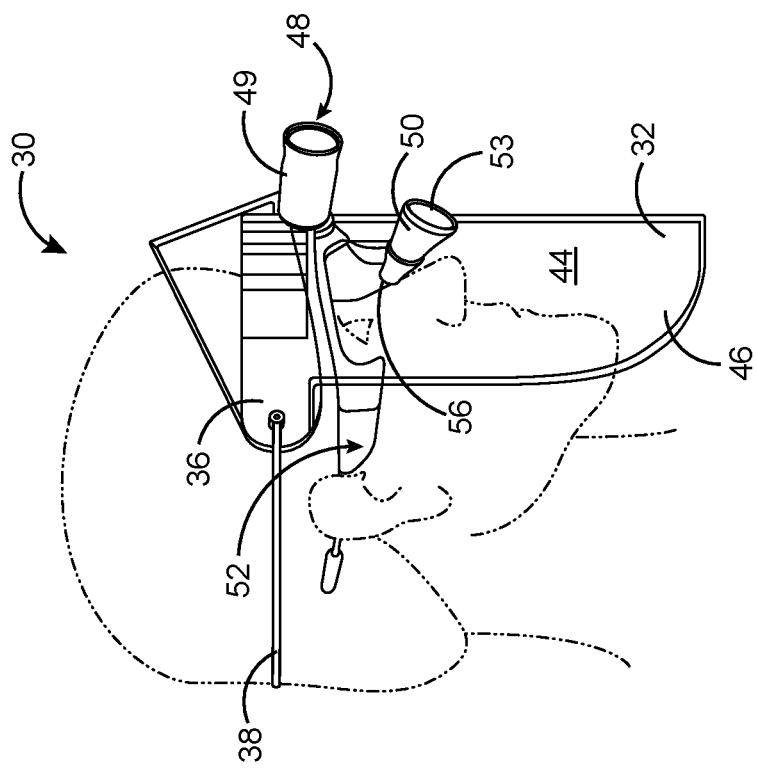
FIG. 4 shows a side view of the face protecting apparatus shaped to accommodate a loupe device and a fiber optic LED light worn by the user in accordance with one embodiment of the present invention.

FIG. 4 shows basic features of the present invention shared by the first and the second prototypes having the frame member 36 and the face shield 32 to protect the care provider while providing an unobstructed use of the fiber optic LED light 48 and the loupe device 52. In FIG. 4, the fiber optic LED light 48 and the loupe device 52 with long barrel magnifiers are shown protruding through a plurality of openings 56 on the face shield 32 from underneath. In addition, the present invention is adaptable to use with a wide variety of fiber optic LED medical headlights, including reversibly attachable headlights.

The face protecting apparatus 30 is adapted for protecting a user's eyes and face while providing unique shield flexibility and combined use with various devices. As illustrated in FIG. 3A, FIG. 3B, FIG. 11A, and FIG. 11 B, and further to the above, the face shield 32 is translucent that covers a user's face while maintaining an unobstructed use of both the fiber optic LED light 48 and the loupe device 52. The face protecting apparatus 30 permits the use of a low-profile fiber optic light 48 in addition to the use of magnification built into lenses of a user's spectacle as shown in FIG. 11A and FIG. 11B.

The plurality of openings 56 on the face shield 32 enables the fiber optic LED light 48, the right optic magnifier 50 and the left optic magnifier 51 (FIG. 11B) worn by the user to protrude therethrough thus enabling the user to wear the face protecting apparatus 30 in combination with the loupe device 52 and the fiber optic LED light 48 without any obstruction. The loupe device 52 and the fiber optic LED light 48 accurately protrude through the plurality of openings 56 utilizing a plurality of connectors 60 such as a grommet as shown in FIG. 5A. The fiber optic LED light 48 is provided with ample space to maintain freedom of movement for the user thereby allowing the user to accurately position the LED light 48 during treatment. In some embodiments, this function is accomplished through the use of the grommets made of rubber or similar material. The grommets 60 allow for a tight seal and an ample flexibility to the fiber optic LED light 48 according to the comfort of the user while treating the patient.

As shown in FIG. 5A, the grommets 60 include bushing-type form factors adaptable to provide mechanically simple design yet providing sufficient support to the face protecting apparatus 10 having different barrel designs.

Further, in some embodiments of the present invention, a plurality of star-cut style grommets 62 is contemplated. FIG. 5B shows examples of the plurality of star-cut flex rubber grommets 62 that can be utilized as an alternative to the bushing type grommets 60. The star-cut grommet 62 provides additional flexibility where required. The star-cut grommets 62 better facilitates a variety of loupe magnifiers requiring wider openings in the plastic face shield 32 to obtain that wider diameter at the end portion of a loupe barrel 53 (see FIG. 4) through the face shield 32 while maintaining a supportive grip to the narrower section of the loupe barrel 53 in its final position. Relatedly, FIG. 5C shows different locations of the plurality of star-cut grommets 62 positioned at the face shield 32. The different locations include a LED grommet location 64 for the fiber optic LED light 48, a left grommet location 66 for the left magnifier 51, and a right grommet location 68 for the right magnifier 50.

Figure 6A:
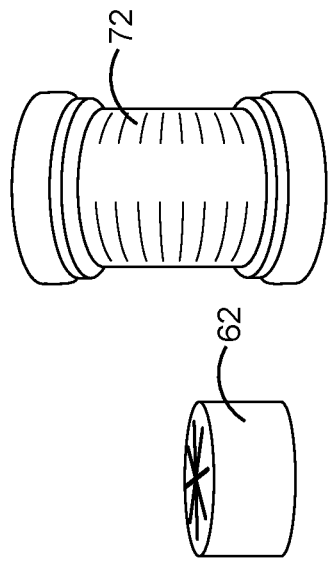
FIG. 6A shows at least one of the plurality of star-cut flex rubber grommets enclosed in a permanently attached protective sheathing in accordance with one embodiment of the present invention.

Preferably, the grommets 60 are designed to convey maximum protection from projectile debris or splatter utilizing the star-cut grommet design that features a thin rubber protective cylindrical sheathing 70 when used in a fully contained and enclosed face shielding 32. This configuration is the most flexible and adaptable design option in that case. FIG. 6A illustrates such an approach, showing the rubber sheathing 70 that is permanently attached to the star-cut grommet 62. In this particular embodiment, the fiber optic LED light 48 or the lope device 52 is pushed through the star-cut barrel from the underneath side of the face shield 32 and through a sleeve of the rubber sheathing. The rubber sheathing 70 provides a barrier from an exposed side of the face shield 32.

Figure 6B:
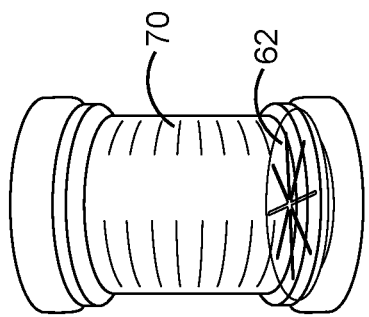
FIG. 6B shows the at least one star-cut flex grommet in a raised state and a disposable rubber sheathing in accordance with one embodiment of the present invention.
Figure 6C:
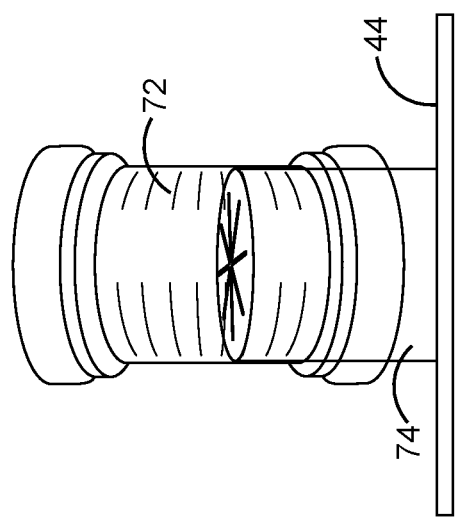
FIG. 6C shows a high-profile star-cut flex grommet used with the disposable rubber sheathing in accordance with one embodiment of the present invention.

An alternative approach for using the star-cut grommet 62 is to use it in a raised state where an external sheathing can be slipped onto the protruding grommet as depicted in FIG. 6B and FIG. 6C. Here, the star-cut flex grommet 62 is used in conjunction with a disposable rubber protective sheathing 72. FIG. 6C shows a high-profile star-cut flex grommet 74 protruded through the planar surface 44 of the face shield 32 used with the disposable rubber protective sheathing 72. One of the primary advantages of this approach is that it provides a means for replacing the rubber sheathing 70 thereby eliminating the hassle and time-intensive process of sanitizing the rubber sheathing 70.

In certain embodiments, the second prototype includes a dual-frame mechanism that allows the face shield 32 to flip up partially or completely, as well as tilt down. The gap between the outer frame and the forehead frame can be closed by affixing a replaceable barrier (such as closed-cell extruded polystyrene foam, etc.) to the inside of the outer frame. In some embodiments, the outer frame is a flat band and the declination angle is formed by virtue of a slotted connection at the point of rotation which results in an exaggerated downward tilt for the purpose of temporarily moving the face shield 32 on and off the area in front of the face. In use, the downward tilt also allows the face shield 32 of the face protecting apparatus 30 to form a seal against the operator's chest or upper neck. Alternately, when the angle of tilt is designed into the injection-molded outer frame, the molded design itself dictates the tilt of the face shield 32 thereby eliminating the need for a slotted mechanism to define the angle. The only up and down flipping in this molded design is for the purpose of sliding the face shield 32 from in front of the face towards the back portion of the head. According to the second prototype approach, the frame member 32 requires flip up either partially or completely, and it will perform in that manner such that the frame member 32 clicks into position and is held there until deliberately moved out of that position.

Figure 12:
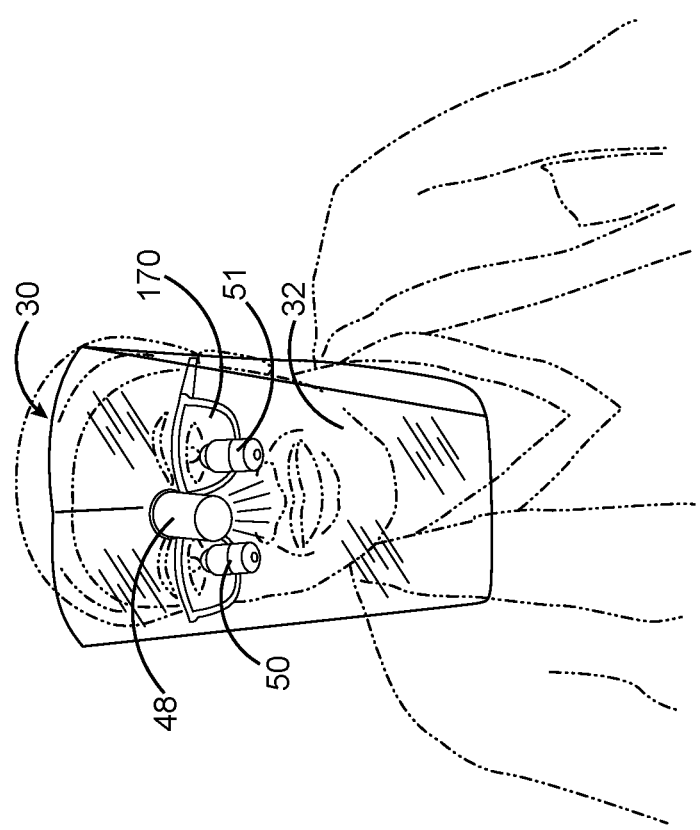
FIG. 12 shows a front perspective view of the face protecting apparatus, illustrating the face shield without an anti-glare element, the plurality of loupe magnifiers, the fiber optic LED light in the active state and the pair of glasses in accordance with one embodiment of the present invention.

As shown in FIG. 11A and FIG. 11B, the second prototype includes at least one anti-glare element 160 integrated into or onto the plastic face shield 32. FIG. 11A and FIG. 11B illustrate the face shield apparatus in use. The apparatus 30 includes the fiber optic LED light 48 in an active state, the loupe device 52, the face shield 32, the securement knobs 34, and a surgical mask 162. FIG. 12 shows a combined use of the face shield 30 without the tinting element, the plurality of loupe magnifiers 50, 51, glasses 170, and the LED light 48 in the active state. Antiglare and eye protecting films can be created in such a way to easily apply and remove while the face shield 32 is in use.

In another aspect of the present invention, the face protecting apparatus 30 is fitted with a system for easy disinfection. The disinfection system includes a plurality of preassembled sets of protective ultra-thin layers of shield that covers both the first and the second prototypes. These protective ultra-thin layers can be affixed to or factory pre-loaded onto the outer face of the face shield 32 prior to treating the patient. The outer layer of the so affixed disinfection barriers may be peeled off after treating patients and/or between patients as needed to maintain a clean patient-facing surface to the face shield 32. When the last preloaded disinfection barrier is removed, a new preloaded shield may be attached to the frame member 36. In certain instances, a stack of layers of peel-off covers may be applied to the face shield 32 while in other instances, the face shield 32 may be provided with a preinstalled layers of peel-off covers.

In another aspect of the present invention, the second prototype includes a clip-on attachment concept that allows the face protecting apparatus 30 (plastic shield 32 and outer frame 36 only) to be adapted to any existing fiber optic headgear frame. This feature allows the face protecting apparatus 30 to be clipped, attached, and/or affixed to the user's already existing headgear apparatus, permitting adaptability with inventory already in the workplace.

The second prototype possesses several advantages. These advantages include, but are not limited to: fitting over existing brands of fiber optic 48 and loupe 52 designs, including a non-glare upper element 40 to counter any reflected light on the plastic face shield 32, flipping up for or easy donning and doffing for quick access to the fiber optic LED light 48 to adjust position or tighten screws, designed to angle toward the chin with the plurality of bilateral creases 46 and the forehead dart member 42 for closer face proximity and enclosure, and having the elongated length enough to easily create a seal at the clinician's chest with slight bending of the neck forward. Further, advantages of the present invention include non-clouding, non-fogging, and disinfecting iterations, a "peel-away" feature where protective layers can be preloaded and easily removed between patients, and a means of attachment to existing fiber optic headgear assemblies.

In one aspect of the present invention, the face shield apparatus contemplates a method for providing physical head protection utilizing the loupe device 52 and the fiber optic LED light 48. FIG. 7A and FIG. 7B depict a head protector 80 in the form of a helmet made of an antimicrobial protective fabric 84. The head protector 80 includes the plastic face shield 32, and a protective neck veil 82. FIG. 7B shows a rear view of the head protector 80. One variation of this configuration incorporates a plurality of helmet openings for the fiber optic LED light 48 and the loupe device 52 along a lower edge of a removable and replaceable layer of an autoclavable Halyard Fabric. The detachable fabric can be worn inside or outside other Personal Protective Equipment (PPE) garments. Another variation of this head protecting configuration, shown in FIG. 7C and FIG. 7D, depicts a fully closed head protector 90 made of cleansable material with the addition of a compartment 94 on top of the fabric for securing a power supply for the fiber optic LED light 48 or other electronic apparatus such as intercom, dictation, ventilation components etc. FIG. 7D shows a rear view of the fully closed head protector 90.

FIG. 7E depicts another configuration of the head protector featuring a ventilated full head protector 100 having a full head neck veil 104 and an external ventilation system 102. The inclusion of the ventilation system 102 along with the face protecting apparatus 30 is very beneficial to the full head protection approach. The basic ventilation system 102 includes a plurality of dedicated air openings towards a rear portion of the head away from the potentially hazardous elements in close proximity to the patient's breathing space. In order to ensure proper separation of the intake and outlet flow of air within the insulated space of the helmet shaped head protector 100, a set of unidirectional air valves 106 are utilized one for each flow direction. These air valves 106 can be installed directly at a port opening in the rear area where a plurality of hose connectors or a filtration canister is located. The air mask is optional in more spacious head protector depicted in FIG. 7E.

Figure 8A:
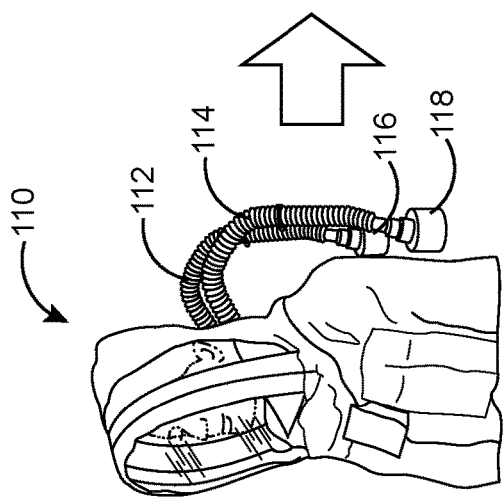
FIG. 8A shows basic components of a standard air ventilation system having a series of air flex hoses and adaptable to use with the face protecting apparatus in accordance with one embodiment of the present invention.
Figure 8B:
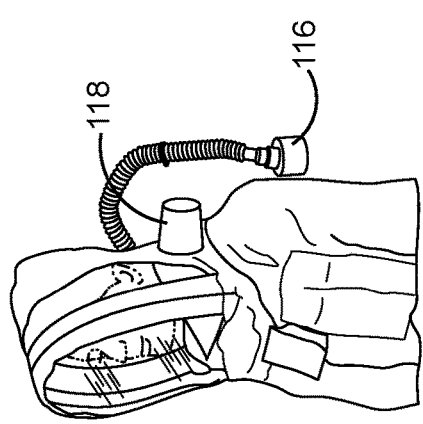
FIG. 8B shows another embodiment of the standard air ventilation system shown in FIG. 8A having an air intake filtration located at a highest possible practical point and an outlet air exhausted downward as close to the ground in accordance with one embodiment of the present invention.
Figure 8C:
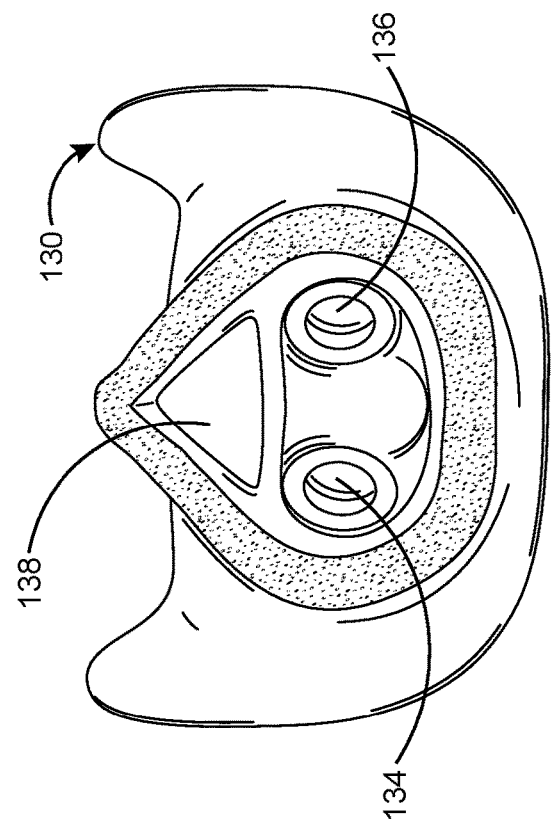
FIG. 8C shows an underneath side of an air ventilation mask having flow paths for both air intake and air outlet and adaptable to use with the face protecting apparatus in accordance with one embodiment of the present invention.

In another configuration of the full head protection concept, a standard ventilation system 110 includes functional elements such as a plurality of dedicated ventilation ports for air intake and air exhaust located at a rear portion of the head protector, an air-intake filtration element 118 and an air-outlet filtration element 116 (optional), an air mask, and a series of air flex hoses including an air inlet hose 114 and an air outlet hose 112 necessary for this specific configuration. If a particular embodiment of the present invention requires the use of an air mask, the valve mechanisms may also be integrated into the mask directly as shown in FIG. 8A. According to several studies, viruses and germs eventually migrate downward towards the ground. Therefore, the preferred location of the air intake filtration element 118 is at a highest possible practical point as clearly illustrated in FIG. 8B. In contrast, the air-outlet filtration element 116 should be exhausted downward as close to the ground as practical as possible as shown in FIG. 8B. The filtration material should ideally be made from an antimicrobial fabric with N-Series or R-Series or P-Series rated. FIG. 8C shows an air mask 130 having several flow paths for both air intake and air outlet and adaptable to use with the face protecting apparatus 30. The air mask 130 includes an air in-take port 134, an air out-take port 136 and a nose bridge support 138.

In certain embodiments of the present invention, the above-mentioned ventilation system 110 can be substituted with a fully operational respirator system. Several varieties of respirators are available on the market ranging from medium sophisticated to most advanced systems. The only requirement is that there should be a source of clean air to connect to and a place where exhaled air is exhausted out at the respirator.

In another aspect of the present invention, the face protecting apparatus 30 is designed as custom fitted. Specifically, in lieu of the configurable version of the face protecting apparatus 30, the present invention may be constructed with the fiber optic LED light 48 and the plurality of loupe magnifiers 50, 51 built directly into the mask and custom fitted to the user just as the loupes are custom fitted presently. In this configuration, the seals would thus be air-tight (not permitting particles greater than 0.3 microns to pass) with no possibility of microbe passage or penetration.

Figure 9B:
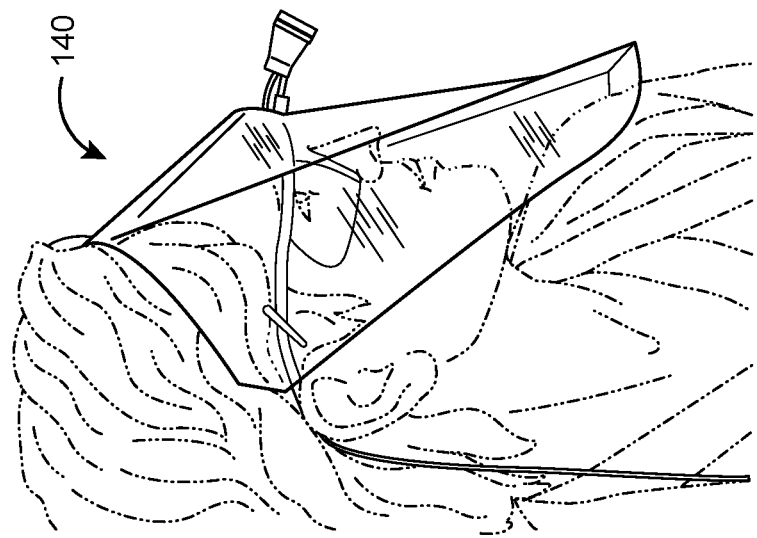
FIG. 9B shows a side perspective view of the disposable version of the face protecting apparatus illustrated in FIG. 9A.
Figure 9A:
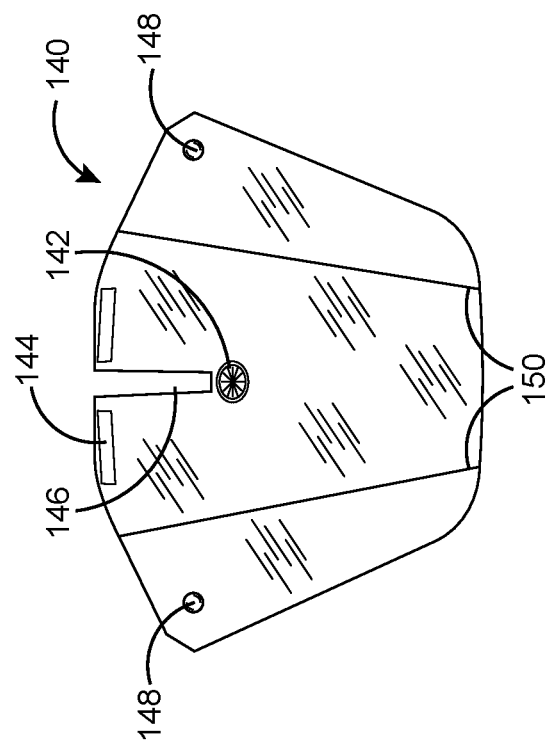
FIG. 9A shows a disposable version of the face protecting apparatus including an acrylic plastic sheet in accordance with one embodiment of the present invention.

In other embodiments, a disposable full face protecting apparatus 140 with loupe support is contemplated with the present invention as illustrated in FIG. 9A. Specifically, during periods of global or national pandemic emergency situations, a disposable form factor offers a quick and cost-effective solution ideal for mass distribution. The disposable version utilizes an approach of using a flattened clear plastic or acrylic sheet die cut to a shape similar to the shape depicted in FIG. 9A. Referring to FIG. 9A, an overlapping fold cut out 146 allows for concave form over the head near the face. Several hook and loop fastener strips 144 and metal snaps 148 or similar methods are used to secure the concave fold and snaps on the elastic bands respectively in an adjustable manner specific to the wearer. A set of pre-scored fold lines 150 guides the user with the location of the folds for side face protection. Specifically, FIG. 9B shows a side perspective view of the disposable full face protecting apparatus 140 worn by the user.

In certain embodiments, the face protecting apparatus 30 can be affixed to the head in the form of an elastomeric headband with a forehead component that holds the top of the face shield 3-4 inches in front of the wearer's eyes. In this manner, the face shield 32 bypasses the projection of the loupe devices 52 and the magnification lenses all together. The plurality of securing members 34 has a rigid and stable component that firmly holds the plastic face shield 32. As described in the above embodiments, the face shield 32 includes the elongated planar surface and the plurality of bilateral creases 46. The plurality of bilateral creases 46 brings the face shield 32 into close proximity to the face and angles it down one inch in front of the chin in the facial dimension. The elongated length of the face shield 32 causes a slight bend of the neck to seal against the wearer's chest. A top portion of the shield 32 includes a head/hair covering that can be affixed to close the open-air channel created by an angle of this iteration thus protecting the hair and the head from pathogenic exposure.

In some embodiments, the face shield 32 is adaptable to flip up and down. When the face shield 32 flips up, a catch is built into a hinge causing it to remain in the up position. In other embodiments, the face shield 32 or visor includes a mount so that the user connects a surgical headlight to the top of the face shield 32 and if corded, a channel may be provided such that the cord may run along and stay in place along the side or sides of the face shield 32. In certain other embodiments, the body of the shield 32 is autoclavable or sturdy enough to wipe and disinfect. The shield portion should be removed and disposable. Alternatively, a configuration is considered in which a fiber optic LED light 48 is reversibly attachable. In yet other embodiments, several reversible and detachable projections may be connected to the face shield 32 and tied to a rear portion of the face protecting apparatus 30 such that the system is fully closed. The same may be done at the opposing end of the face protecting apparatus 30. In all iterations, the apparatus 30 is effective at filtering 0.03-micron particles.

In some embodiments, the face protecting apparatus 30 fits over all existing brands of fiber optic and/or loupe designs. In other embodiments, the face protecting apparatus 30 includes: a non-glare upper element 160 to counter the reflected light on the plastic face shield 32, may flip up for easy access to fiber optic light to adjust position or tighten screws, may be designed to angle the chin for closer face proximity and enclosure, is long enough to easily create a seal at the clinician's chest with slight bending of the neck forward, and may include non-clouding, non-fogging, and/or disinfecting materials with standard clinical grade disinfectants. Finally, as described above, the face protecting apparatus 30 may also include a "Tear-off" feature where protective layers can be preloaded and easily removed between patients in addition to a reversible means of attachment to existing fiber optic headgear assemblies.

FIGS. 10A and 10B clearly illustrate the plurality of bilateral creases 46, the elongated face shield 32 and the dart member 42. The bilateral creases 46 and the forehead dart 42 bring the face shield 32 into closer proximity with the face. In one configuration of the preferred embodiment, the plurality of bilateral angled creases 46 has an inclination of 45 degrees. The dart 42 at the forehead creates concave anatomy that conforms to the face such that the assembly better encapsulates, adheres to, and protects the face of the user. Regarding the narrow gap between the shield and the user's chest, majority of prior art systems include a wide gap where aerosols are most prevalently generated during a dental procedure. The elongated and planar plastic face shield 32 forms the seal against the wearer's chest when his or her head is tilted down in operation. The loupe device 52 and the fiber optic LED light 48 are accurately protruded through the plurality of openings 56 utilizing the plurality of grommets 60. The plurality of securing members 34 connects the face shield 32 to the rigid head frame 36 of a head band.

Figure 13B:
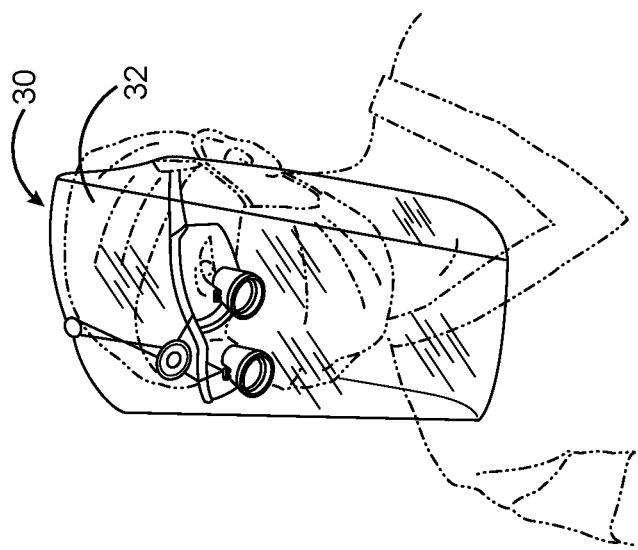
FIG. 13B shows a side perspective view of the face protecting apparatus, illustrating a closed state of the face shield without the tinting element in accordance with one embodiment of the present invention.
Figure 13A:
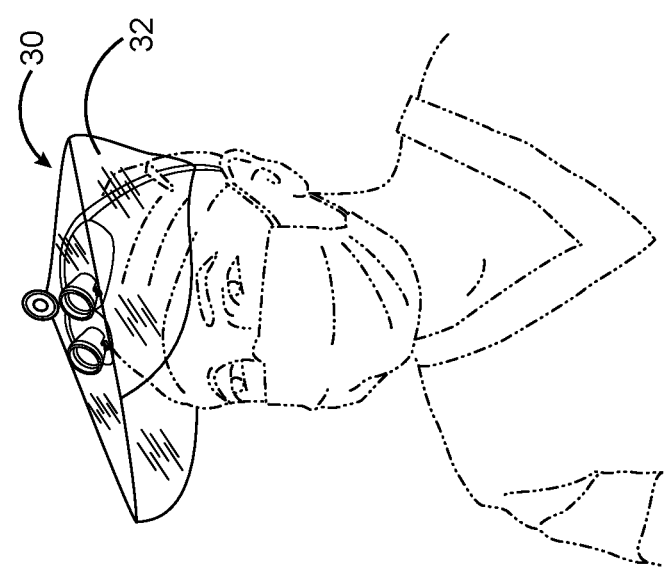
FIG. 13A shows a side perspective view of the face protecting apparatus, illustrating an open state of the face shield without a tinting element in accordance with one embodiment of the present invention.

FIG. 13A shows an open state (not in use) of the face shield 32 without the tinting element. FIG. 13B shows a closed state (in use) of the face shield 32 without the tinting element.

Figure 14B:
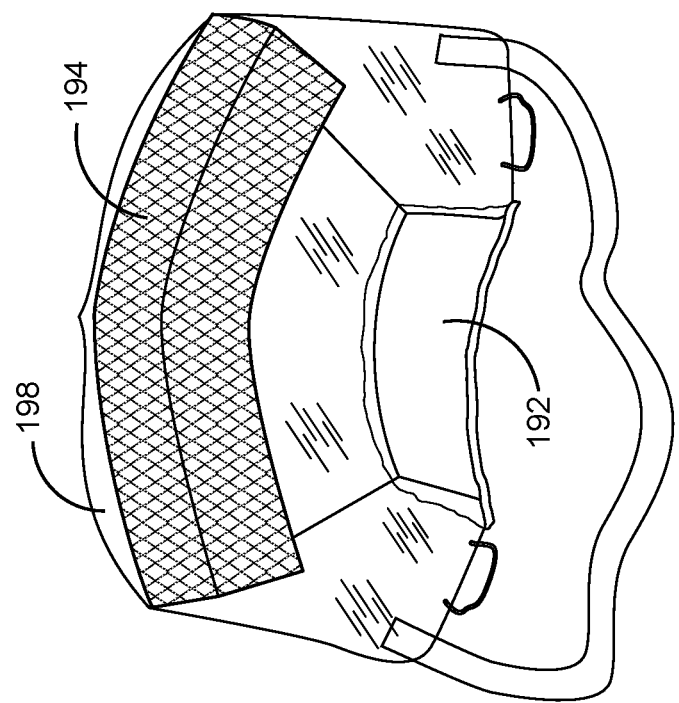
FIG. 14B shows a rear view of the face shield attached with the filter illustrated in FIG. 14A in accordance with one embodiment of the present invention.
Figure 14A:
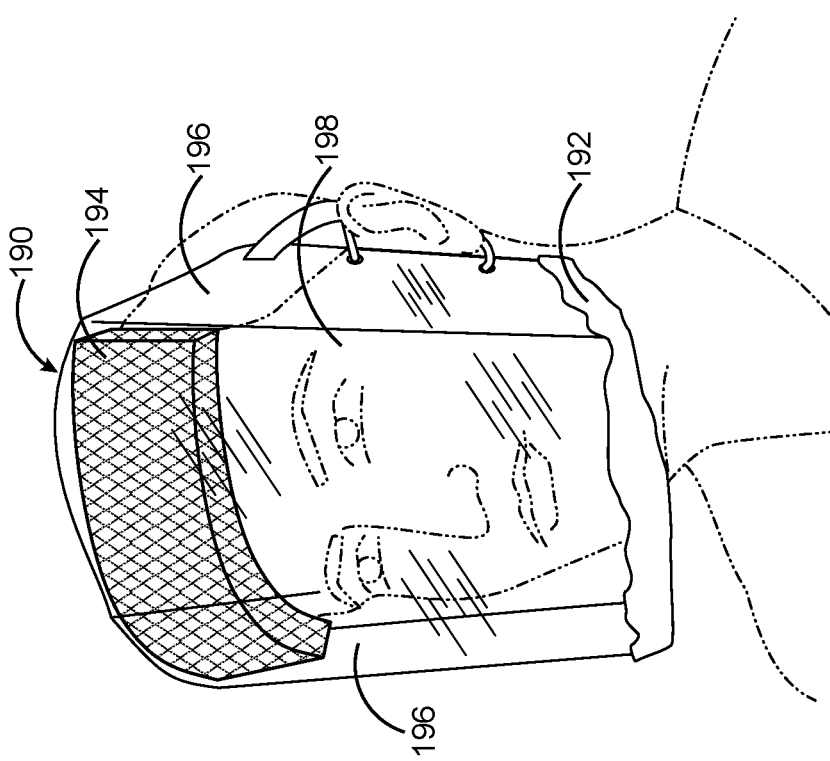
FIG. 14A shows a side perspective view of the face protecting apparatus having a filter at a bottom portion of the face shield in accordance with one embodiment of the present invention.
Figure 14C:
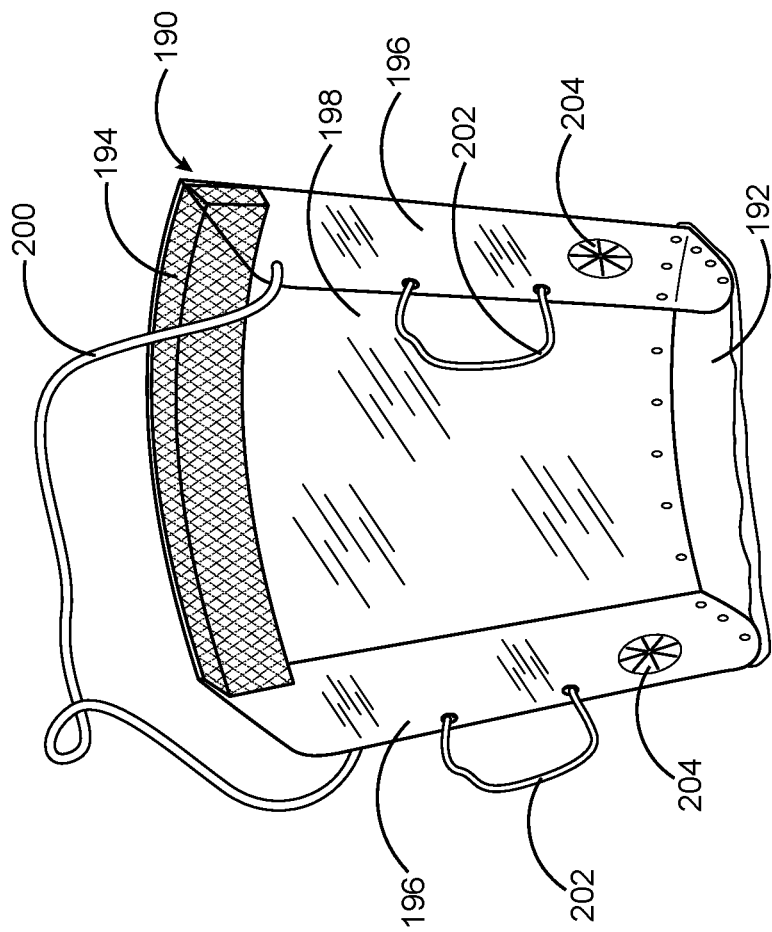
FIG. 14C shows components of the face protecting apparatus, illustrating the face shield attached with the filter shown in FIG. 14A and FIG. 14B in accordance with one embodiment of the present invention.

FIG. 14A shows yet another embodiment of the face protecting apparatus 190 having a filter 192 at a bottom portion of the face shield 198. The filter 192 is added under the chin so that air drawn inside from under the chin gets filtered. The face protecting apparatus 190 includes a foam forehead support 194. There are two sub-embodiments for this configuration. In the first sub-embodiment, the plurality of bilateral creases 196 does not touch the face of the user. This embodiment includes a one way valve at the top portion to allow air to escape. But, in the second sub-embodiment, the plurality of bilateral creases 196 touches the face and there are three one way valves in which two valves are bilaterally positioned and one valve at top. FIG. 14B shows a rear view of the filter 192 attached to the face shield 198. FIG. 14C illustrates components of the face protecting apparatus 190 attached with the filter 192. The face shield 198 is secured to the head utilizing an elastic head securing member 200. The foam forehead support 194 is attached to the upper portion of the face shield 198. This embodiment is shaped to accommodate a single frame support or a double fame support. The plurality of bilateral creases 196 brings the shield 198 into close proximity to the face. A pair of ear loops 202 enables the user to secure the face shield 198 on user's ears. The filter 192 attached at the user's chin should be changed to inhibit entry of pathogens. A one way valve 204 filters air coming in and allows the exhaust air to prevent fogging.

Further to and summarizing the above, the present invention contemplates another embodiment including the frame member 36 for the user's head and the removable face shield 32 supported by the frame member 36. The protective face shield 32 is removably supported in an opening of the frame member 36 by a channel, without the use of fasteners. Since the face shield 32 lacks fasteners, it is easy to remove and replace, even with the use of gloves. In one embodiment, the frame member 36 is molded as a single, unitary member and includes an upper detent, a lower detent and a channel formed between a lip and the frame member 36. The channel receives an edge of the protective face shield 32 in order to hold the face shield 32 within the frame member 36. In another embodiment, the frame member 36 is pivotally supported on a support structure such that the frame member 36 can be moved between an upper (out of use) and a lower (in use) position, and may further include an adjustable mounting member so that the frame member 36 can be selectively spaced relative to the user's head.

As described above, the present invention also effectively combines subcomponents of the face shield 32 such as the loupe device 52 with the plurality of loupe magnifiers 50, 51 and the fiber optic LED light 48 in a combination conducive to the proper performance of each component for its intended use without onerous reconfiguration. For example, the plurality of openings 56 in the face shield 32 for the plurality of loupe magnifiers 50, 51 provides a solution for longer optical barrels. Conversely, the plurality of openings 56 may be eliminated for the plurality of loupe magnifiers 50, 51 when using shorter optical or magnifying barrels. Notably, the design may also include punches and templates allowing the user to customize these components without compromising the safety of the user. Further, the unique bilateral 45-degree creases 46 create a concave configuration to the plastic shield 32, allowing close adaptation and proximity to the wearer's face thus offering added isolation and protection from splatter and aerosolized debris. The elongated length of the face shield 32 is sufficient to touch the wearer's chest with only a slight, comfortable bend of the neck, thus offering more of a seal and barrier to ejected debris from a drill or aerosol producing instrument in use by the user.

One of ordinary skill in the art will recognize that additional embodiments are also possible without departing from the teachings of the present invention. This detailed description, and particularly the specific details of the exemplary embodiments disclosed herein, is given primarily for clarity of understanding, and no unnecessary limitations are to be understood therefrom, for modifications will become obvious to those skilled in the art upon reading this disclosure and may be made without departing from the spirit or scope of the claimed invention.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The foregoing description of the preferred embodiment of the present invention has been presented for the purpose of illustration and description. It is not intended to be exhaustive or to limit the invention to the precise form disclosed. Many modifications and variations are possible in light of the above teachings. It is intended that the scope of the present invention to not be limited by this detailed description, but by the claims and the equivalents to the claims appended hereto.

What is claimed is:

1. A face protecting apparatus comprising:
    a frame member configured to be secured to the head of a user;
    a removable face shield connected to the frame member and having an elongated planar surface adaptable to create a seal at the user's chest when the user bends forward thereby providing a protective barrier to ejected debris from an aerosol producing instrument in use by the user, the face shield comprising:
        a plurality of bilateral angled creases to provide a concave configuration to the face shield that brings the face shield into close proximity to the face of the user; and
        a plurality of openings to allow a fiber optic LED light and a plurality of loupe magnifiers of a loupe device worn by the user to protrude therethrough thus enabling the user to wear the face protecting apparatus in combination with the loupe device and the fiber optic LED light without any obstruction while treating a patient;
    a dart member at a centerline of an upper portion of the face shield that forms a concave anatomy inside the face shield to protect the face of the user from hazardous materials; and
    at least one anti-glare element at the face shield to mitigate eye strain caused by the reflected light from the fiber optic LED light against the face shield;
    whereby the seal created by the elongated planar surface of the face shield and the concave configuration provided by the plurality of bilateral angled creases and the dart member protect and isolate the user from droplets and solids containing bacteria, viruses, and other hazardous materials;
    wherein the loupe device and the fiber optic LED light protrude through the plurality of openings utilizing a plurality of connectors.

2. The face protecting apparatus of claim 1 wherein the frame member is configured to be secured to the head of the user utilizing at least one fastening member.

3. The face protecting apparatus of claim 1 wherein the face shield is connected to the frame member utilizing a plurality of securing members.

4. The face protecting apparatus of claim 1 wherein the concave anatomy created by the dart member conforms to the face of the user such that the face shield adheres to, encapsulates, and protects the face of the user from aerosols and fluids expelled by the patient or during the course of treating a patient.

5. The face protecting apparatus of claim 1 wherein the apparatus is shaped to accommodate a ventilation system to protect the user from the hazardous materials in close proximity to the breathing space of the user.

6. A face protecting apparatus comprising:
    a frame member configured to be secured to the head of a user utilizing at least one fastening member;
    a removable face shield connected to the frame member utilizing a plurality of securing members and having an elongated planar surface adaptable to create a seal at the user's chest when the user bends forward thereby providing a barrier to ejected debris from an aerosol producing instrument in use by the user, the face shield comprising:
        a plurality of bilateral angled creases to provide a concave configuration to the face shield that brings the face shield into close proximity to the face of the user; and
        a plurality of openings to enable a fiber optic LED light and a plurality of loupe magnifiers of a loupe device worn by the user to protrude therethrough thus enabling the user to wear the face protecting apparatus in combination with the loupe device and the fiber optic LED light without any obstruction while treating a patient;
    a dart member at a centerline of an upper portion of the face shield that forms a concave anatomy inside the face shield to protect the face of the user from hazardous materials;
    a plurality of connectors for accurately positioning the loupe device and the fiber optic LED light on the face shield; and at least one anti-glare element at the face shield to mitigate eye strain caused by the reflected light from the fiber optic LED light against the face shield;

whereby the seal created by the elongated planar surface of the face shield and the concave configuration provided by the plurality of bilateral angled creases and the dart member protect and isolate the user from droplets and solids containing bacteria, viruses, and other hazardous materials;

wherein the loupe device and the fiber optic LED light protrude through the plurality of openings utilizing a plurality of connectors.

7. The face protecting apparatus of claim 6 wherein the plurality of loupe magnifiers includes a right optic magnifier and a left optic magnifier.

8. The face protecting apparatus of claim 6 wherein the plurality of connectors includes a plurality of grommets that allows for a tight seal and an ample flexibility to the fiber optic LED light according to the comfort of the user while treating the patient.

9. A face protecting apparatus comprising:

a frame member configured to be secured to the head of a user; and a removable face shield having an elongated planar surface and connected to the frame member, the face shield comprising a plurality of bilateral angled creases, and a plurality of openings, the elongated planar surface creating a seal at the user's chest when the user bends forward thereby providing a protective barrier to ejected debris from an aerosol producing instrument in use by the user, the plurality of bilateral angled creases providing a concave configuration to the face shield that brings the face shield into close proximity to the face of the user, the plurality of openings at the face shield enabling a fiber optic LED light and a plurality of loupe magnifiers of a loupe device worn by the user to protrude therethrough thus enabling the user to wear the face protecting apparatus in combination with the loupe device and the fiber optic LED light without any obstruction;

whereby the seal created by the elongated planar surface of the face shield and the concave configuration provided by the plurality of bilateral angled creases protects and isolates the user from droplets and solids containing bacteria, viruses, and other hazardous materials;

wherein the loupe device and the fiber optic LED light protrude through the plurality of openings utilizing a plurality of connectors.

10. The face protecting apparatus of claim 9 wherein the frame member is configured to be secured to the head of the user utilizing at least one fastening member.

11. The face protecting apparatus of claim 9 wherein the face shield is connected to the frame member utilizing a plurality of securing members.

12. The face protecting apparatus of claim 9 wherein the plurality of loupe magnifiers includes a right optic magnifier and a left optic magnifier.

13. The face protecting apparatus of claim 9 further comprising a dart member at a centerline of an upper portion of the face shield that forms a concave anatomy inside the face shield that better conforms to the face such that the face shield encapsulates, adheres to and protects the face of the user from the hazardous materials such as aerosols and fluids expelled by a patient or during the course of treating a patient.

14. The face protecting apparatus of claim 9 wherein the plurality of connectors includes a plurality of grommets that allows for a tight seal and an ample flexibility to the fiber optic LED light according to the comfort of the user while treating the patient.

15. The face protecting apparatus of claim 9 wherein the face shield is adaptable to integrate with at least one anti-glare element to mitigate eye strain caused by the reflected light from the fiber optic LED light against the face shield.

16. The face protecting apparatus of claim 9 wherein the apparatus is shaped to accommodate a ventilation system to protect the user in close proximity to a breathing space of the user.

* * * * *